US00PP37135P2

(12) United States Plant Patent
Huber

(10) Patent No.: US PP37,135 P2
(45) Date of Patent: Dec. 9, 2025

(54) ***DAHLIA* PLANT NAMED 'LeeAnn's FD43C'**

(50) Latin Name: *Dahlia hybrida*
Varietal Denomination: 'LeeAnn's FD43C'

(71) Applicant: LeeAnn Huber, Greencastle, PA (US)

(72) Inventor: LeeAnn Huber, Greencastle, PA (US)

(73) Assignee: Coseytown Flowers llc, State Line, PA (US)

( * ) Notice: Subject to any disclaimer, the term of this patent is extended or adjusted under 35 U.S.C. 154(b) by 0 days.

(21) Appl. No.: 19/028,261

(22) Filed: Jan. 17, 2025

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
See application file for complete search history.

(56) References Cited

U.S. PATENT DOCUMENTS

PP19,225 P2 * 9/2008 van Haaster ..... A01H 6/14
Plt./321

* cited by examiner

*Primary Examiner* — Susan Mccormick Ewoldt
*Assistant Examiner* — Zachariah Allan Kay

(57) ABSTRACT

A new and distinct cultivar of *Dahlia* plant named 'LeeAnn's FD43C' is disclosed, characterized by medium pink, formal decorative form blooms with coral shading on plants with a strong, upright growth habit. Flowers are held above the foliage canopy and have a consistent quality throughout the growing season. Flowering stems have an above average strength with a firm blossom attachment. Inflorescences have strong postproduction quality. The new variety is a *Dahlia* typically produced for cut flower purposes, or garden or landscape.

2 Drawing Sheets

Figure 1:
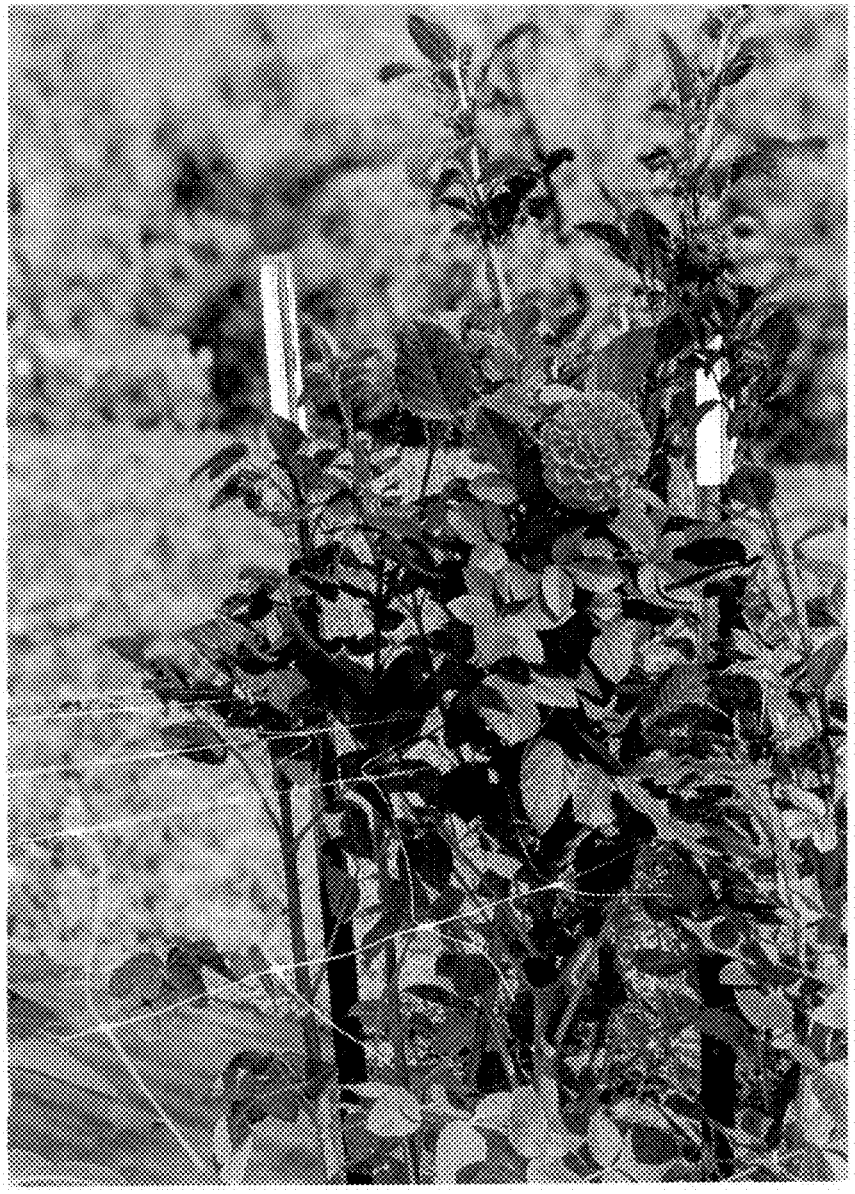

Latin name of the genus and species: *Dahlia hybrida.*
Variety denomination: 'LeeAnn's FD43C'.

BACKGROUND OF THE INVENTION

The new *Dahlia* cultivar is a product of a planned breeding program conducted by the inventor, in Greencastle, Pennsylvania. The objective of the breeding program was to produce new *Dahlia* varieties with improved performance in open field conditions and produce cut flowers suitable for transport and sale. The open-pollination resulting in this new variety was made during the Fall of 2020.

The seed parent is the unpatented, variety of *Dahlia* 'Sonia'. The pollen parent is unidentified. 'LeeAnn's FD43C' was intentionally selected in the Summer of 2021 based on the criteria of strong, upright growth, as well as free branching and flowers held above the leaf canopy. The new cultivar was selected in Greencastle, Pennsylvania.

Asexual reproduction of the new cultivar was first performed by root divisions by the inventor in Greencastle, Pennsylvania in the Spring of 2022 and has shown that the unique features of this cultivar are stable and reproduced true to type in successive generations.

SUMMARY OF THE INVENTION

The cultivar 'LeeAnn's FD43C' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LeeAnn's FD43C' These characteristics in combination distinguish 'LeeAnn's FD43C' as a new and distinct *Dahlia* cultivar:

1. Strong, upright growth habit requiring minimal to no physical structural support in the field.
2. Free branching.
3. Consistency of bloom quality throughout the growing season.
4. Flower held above the leaf canopy.
5. Strong flowering stems/peduncles. Stem/peduncle strength is measured by assessing if any flexion occurs on harvested flower stems of 35 to 40 cm when the stem is given a brief, firm shake. Any stems which flex are considered average, stems which show damage are below average and stems which remain inflexible are above average and considered strong.
6. Firm blossom attachment.
7. Medium pink with coral shading formal inflorescence.
8. Strong postproduction inflorescence quality as a cut flower of approximately a week, depending on environmental conditions.

PARENT COMPARISON

Plants of the new cultivar 'LeeAnn's FD43C' are similar to plants of the seed parent, in some horticultural characteristics, however, plants of the new cultivar 'LeeAnn's FD43C' differ in the following;

1 'Sonia' is lavender in color; the new cultivar is medium pink with coral shades.
2. 'Sonia' inflorescence bloom size is smaller than 'LeeAnn's FD43C'.

3. Bloom form of 'Sonia' form is considered to be a ball form; the new cultivar has a formal decorative form bloom.
4. Plant height of 'Sonia' is on average shorter than 'LeeAnn's FD43C'.

The pollen parent cannot be identified with certainty.

COMMERCIAL COMPARISON

Plants of the new cultivar 'LeeAnn's FD43C' are comparable to the variety *Dahlia* 'Chewy', unpatented. The two *Dahlia* varieties are similar in most horticultural characteristics; however, the new variety 'LeeAnn's FD43C' differs in the following:

1. 'LeeAnn's FD43C' plant height is around 5 feet; 'Chewy's plant height is around 3.5 feet.
2. 'Chewy' bloom color is orange/bronze with a purple hue; the new cultivar has a medium pink with salmon tones bloom color.
3. 'Chewy' has a shorter lateral branch length.

BRIEF DESCRIPTION OF THE PHOTOGRAPHS

The accompanying photograph in FIG. 1 illustrates in full color a typical flowering plant of 'LeeAnn's FD43C' grown outdoors, in the ground under cut flower production conditions. Age of the plant photographed is approximately 130 days from a rooted cutting.

Figure 2:
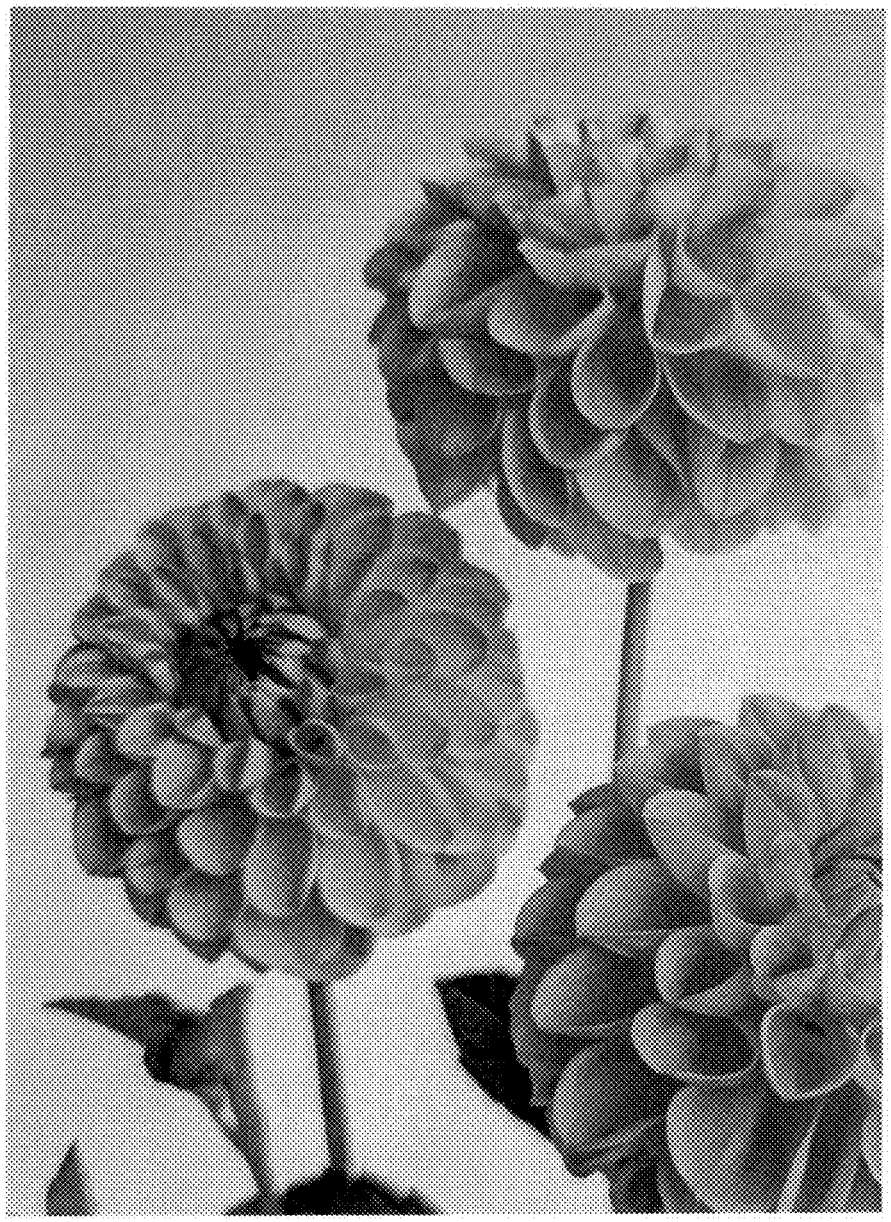

FIG. 2 illustrates a close-up of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society R.H.S. Colour Chart 2015 except where general terms of ordinary dictionary significance are used. The following observations and measurements describe 'LeeAnn's FD43C' plants grown outdoors, in production cut flower rows in Greencastle, PA. The average growing season for outdoor cut flower production runs from May through mid-October or 24 weeks. The terminal bud is pinched off the *Dahlia* around 4-6 weeks of age. Temperatures ranged from about 23° C. to 39° C. during the day and 7° C. to 23° C. at night. General light conditions are bright, normal sunlight. Botanical data was collected between May and September. Measurements and numerical values represent averages of typical plant types.

Botanical classification: *Dahlia hybrida* 'LeeAnn's FD43C'.

PROPAGATION

Time to initiate roots: (March) Winter: 5 to 10 days at approximately 21° C.

Root description: Freely branching, fine rootlets with canescent hairs.

PLANT

Plant type: Herbaceous flowering perennial.

*Plant height.*—59.9 inches.

*Plant spread.*—21.5 inches.

*Lateral branch length.*—34.1 inches.

*Lateral branch diameter base.*—17.3 mm.

*Lateral branch diameter apex.*—13.9 mm.

$2^{nd}$ *internode length.*—205.7 mm.

*Angle of bloom stem from lateral branch average.*—10.4 deg.

*Branch strength.*—Exceptional, resistant to breakage from environmental factors.

*Branch texture.*—Semi-glossy, smooth.

*Branch color.*—Near RHS Yellow-Green 146B tinted with Greyed-Purple 187A.

FOLIAGE

Leaf:

*Arrangement.*—Leaves opposite; leaves may be single, or composite with three or five leaflets.

*Shape.*—Ovate.

*Apex.*—Acute.

*Base.*—Aequilateral.

*Margin.*—Serrated.

*Length.*—Single leaves: about 83 mm. Compound leaves with three leaflets: Average 123.3 mm. Compound leaves with five leaflets: average 161.9 mm.

*Width.*—Single leaves: average 41.3 mm. Compound leaves with three leaflets: average 107.4 mm. Compound leaves with five leaflets: average 137.4 mm.

*Venation pattern.*—Pinnate.

*Texture.*—Upper surface: Smooth. Lower surface: Small, even hispidulous hairs.

*Leaf color.*—Developing foliage: Upper Surface Green NN137A. Lower Surface Green 137B. Fully developed: Upper Surface Green NN137A. Lower Surface 148C.

*Petiole length.*—Single leaves: About 18.7 mm. Compound leaves with three leaflets: about 60.5 mm. Compound leaves with five leaflets: about 71.4 mm.

*Petiole diameter.*—Single leaves: about 2.74 mm. Compound leaves with three leaflets: about 3.2 mm. Compound leaves with five leaflets: about 3.8 mm.

*Petiole texture.*—Upper and lower surfaces — smooth and glabrous.

*Petiole color.*—Upper Surface: Yellow-Green 144B. Lower surface: Yellow-Green 144B.

Stipule: Not present.

FLOWER

Days to flowering from rooted cutting: Plants begin to bloom around 80 days after planting; continuously blooming until the season ending frost in Pennsylvania while maintaining good ray floret count and inflorescence form.

Natural flowering season: During frost free days and nights beginning late April/early May through end of September or early October.

Inflorescence and flower type and habit: Formal decorative form *Dahlia* with ray and disc florets positioned above the foliage on very strong peduncles with an upright to 45° blossom position.

Rate of flower opening: 15 to 18 days from bud to fully opened flower.

Flower longevity on plant: Inflorescence maintains good substance (attractive color with good moisture content) on the plant for about 18 days.

Flower longevity as a cut flower: For about 5-7 days as a cut flower (fresh water at room temperature).

Flowers per plant: Average 9 at one time.
Persistent or self-cleaning: Self Cleaning.
Inflorescence:
*Bloom position*.—positioned above the foliage on the strong peduncles (stalk) with upright to slightly outwardly face.
*Flower scent*.—not fragrant.
Inflorescence bud:
*Shape*.—Oblate.
*Texture*.—Glabrous.
*Appearance*.—Semi-glossy.
*Color*.—Yellow-Green N144A.
*Height*.—12.7 mm.
*Diameter*.—19.3 mm.
Inflorescence size:
*Diameter*.—About 77.2 mm.
*Height or depth*.—About 53.6 mm.
*Receptacle diameter*.—About 7.5 mm.
Ray florets:
*Length*.—About 31.7 mm.
*Width*.—About 22.3 mm.
*Shape*.—Oval.
*Apex*.—Obtuse.
*Base*.—Rounded.
*Aspect*.—Initially upright to reflexed to the peduncle, cupped.
*Texture*.—Upper surface-Smooth, velvety with gold diamond dust, velvety. Lower surface-Smooth, glabrous, white diamond dust, velvety.
Number of ray florets per inflorescence.—About 224 arranged in 15 whorls.
*Color*.—Fully opened: Upper Surface: Base Green-Yellow 1B. Mid Red 40B, Apex Red 43B. Light flush Orange-Red 33C in center. Lower Surface: Base Green-Yellow 1B. Mid to Apex Red 39B. Light flush Orange-Red 33C in center. When opening: Upper Surface: Base Yellow 3A. Mid Red 41C. Apex Red 43C. Overall flush Orange-Red 33C. Lower Surface: Base Yellow 3A. Mid Red 54C and 54D. Overall flush Orange-Red 33D.
Disc florets:
*Disc diameter*.—Average 8.2 mm.
*Shape*.—Tubular.
*Apex*.—Dentate.
*Length*.—About 8.2 mm.
*Diameter, base*.—About 1 mm.
*Number of disc florets per inflorescence*.—Average 26.
*Immature color*.—Apex Yellow 3B, mid section Yellow-Orange 17A, base Yellow 2A.
Phyllaries:
*Quantity per inflorescence*.—Average 8.
*Length*.—About 15.2 mm.
*Width*.—About 6.7 mm.
*Arrangement*.—Whorl.
*Shape*.—Obovate.
*Apex*.—Acute.
*Base*.—Attenuate.
*Margin*.—Entire.
*Texture*.—Upper surface: Smooth, glabrous, satiny. Lower surface: Smooth, glabrous, satiny.
*Color*.—Upper Surface 137C, Lower Surface 137B.
Peduncles:
*Strength of stem*.—Exceptionally strong. Peduncle strength is measured by assessing if any flexion occurs on harvested flower stems (peduncles) of 35 to 40 cm when the stem is given a brief, firm shake. Any stems which flex are considered average, stems which show damage are below average and stems which remain inflexible are above average and considered strong.
*Aspect*.—Mostly upright. Angle of bloom from lateral branch 12-24 degrees.
*Texture*.—Smooth, glabrous.
*Color*.—Yellow-Green 144C.
*Length*.—23 cm.
*Diameter at base*.—9.5 mm.
*Diameter at apex*.—3.7 mm.

REPRODUCTIVE ORGANS

Stamen quantity per disc floret: 5.
*Stamen attachment*.—Filament adnate to ventral surface of corolla.
*Stamen length*.—About 9.1 mm.
*Anther shape*.—Linear.
*Anther length*.—About 4.7 mm.
*Anther color*.—Yellow-Orange 23B.
*Pollen amount*.—Present.
*Pollen color*.—Yellow-Orange 24A.
*Pistil quantity per disc floret*.—1.
*Pistil length*.—About 16.2 mm.
*Stigma shape*.—Bifurcate.
*Stigma form*.—Plumose.
*Stigma length*.—About 3.3 mm.
*Stigma width*.—About 0.6 mm.
*Stigma color*.—Yellow 9B.
*Ovary position*.—Inferior.
*Ovary shape*.—Truncate.
*Ovary color*.—Yellow-Green 154D.
*Ovary length*.—About 2.3 mm.
*Ovary width*.—About 1 mm.
Ray florets: No reproductive structures present.

OTHER CHARACTERISTICS

Fruit/seed:
*Seed length*.—9 mm.
*Seed width*.—2.7 mm.
*Seed color*.—Brown 200A.
Disease/pest resistance: Neither resistance nor susceptibility to normal diseases and pests of *Dahlia* has been observed.
Weather and climate performance: Plants of the new *Dahlia* have excellent tolerance to heat and high UV index, resisting wilting and fading in field grown conditions. Daylight length has minimal effects on bud and bloom production, maintaining cut flower output into late season light and weather conditions.
Temperature range: Grown in any zone as an annual. Can be overwintered in Zone 6 and 7 with protective mulch. Can be perennialized in zones 8 and above.

What is claimed is:

1. A new and distinct cultivar of *Dahlia* plant named 'LeeAnn's FD43C' as herein illustrated and described.

* * * * *